United States Patent [19]

Mollenhauer et al.

[11] Patent Number: 5,433,603

[45] Date of Patent: Jul. 18, 1995

[54] METHOD OF ORTHODONTIC TREATMENT

[76] Inventors: Barry Mollenhauer, 299 Upper Heidelberg Road, Ivanhoe, 3079, Victoria; Arthur J. Wilcock, Kinglake Road & Hill Street, Whittlesea, 3757, Victoria, both of Australia

[21] Appl. No.: 216,117

[22] Filed: Mar. 21, 1994

Related U.S. Application Data

[62] Division of Ser. No. 691,007, filed as PCT/AU89/00541, Dec. 19, 1989, abandoned.

[30] Foreign Application Priority Data

Dec. 19, 1988 [AU] Australia ............... PJ2022
Apr. 14, 1989 [AU] Australia ............... PJ3714

[51] Int. Cl.⁶ .................................................. A61C 3/00
[52] U.S. Cl. ........................................... 433/24; 433/20
[58] Field of Search ..................................... 433/20, 24

[56] References Cited

U.S. PATENT DOCUMENTS

| | | | |
|---|---|---|---|
| 4,037,324 | 7/1977 | Andreasen | 433/20 |
| 4,040,129 | 8/1977 | Steinemann et al. | 420/420 |
| 4,097,993 | 7/1978 | Andrews | 433/20 |
| 4,197,643 | 4/1980 | Burstone et al. | 433/20 |
| 4,412,819 | 11/1983 | Cannon | 433/20 |
| 4,415,375 | 11/1983 | Lederich | 148/11.5 F |
| 4,645,453 | 2/1987 | Nizmick | 433/173 |
| 4,830,823 | 5/1989 | Nakamura | 420/420 |

FOREIGN PATENT DOCUMENTS

| | | | |
|---|---|---|---|
| 0202031 | 11/1986 | European Pat. Off. | C23F 3/06 |
| 0302717 | 2/1989 | European Pat. Off. | A61F 2/30 |
| 2203755 | 10/1988 | United Kingdom | C22C 14/00 |

OTHER PUBLICATIONS

Donachie, Titanium A Technical Guide 1988 pp. 215–216, 28–36.
Kerr, Effect of Hydrogen as Temporary Alloying Element Ti-6Al-4V, 1985, pp. 1077–1087.
Titanium International-Wire Reports 1987–1988 Chemical analysis and mechanical properties.
Metals Handbook—8th Ed. 1961 pp. 1148–1149.
Metals Handbook—9th Ed. 1980 p. 358.

*Primary Examiner*—Nicholas D. Lucchesi
*Attorney, Agent, or Firm*—Harrison & Egbert

[57] ABSTRACT

A method for treatment of orthodontic wire located in a patient's mouth, the wire containing a titanium alloy having either an alpha/beta crystalline structure or a near alpha crystalline structure. The alloy preferably comprises greater than 5% alpha stabilizing components and is maintained below its beta transus. The wire is exposed to an aqueous hydrogen contributing substance over a period of time in the patient's mouth so as to progressively harden or stiffen the wire over that period of time to maintain or increase the force applied by the wire on teeth of the patient.

16 Claims, No Drawings

METHOD OF ORTHODONTIC TREATMENT

This is a divisional of application Ser. No. 07/691,007, filed on as PCT/AU89/00541, Dec. 19, 1989, now abandoned.

This invention relates to materials for medical, dental or veterinary use, such as for use in orthodontics and particularly to orthodontic wires and appliances, methods of treatment of orthodontic wire, methods of fabricating orthodontic appliances, and methods of orthodontic treatment.

Presently orthodontic wires of varying compositions and properties are known. In general, the presently used orthodontic wire compositions and/or their methods of storage, handling and use result in loss of desirable properties to varying degrees, or the wires have some undesirable properties. For example, some alloys, especially Elgiloy (cobalt-chrome-nickel), will show some softening properties in the patient's mouth over a period of time.

It has been proposed to use beta titanium alloy for orthodontic wire. For example, in U.S. Pat. No. 4,197.643 in the name of Burstone there is disclosed the concept of using a beta titanium alloy for the production of orthodontic wire. Beta titanium alloy has a body centred cubic crystalline structure. The advantage claimed for the beta titanium alloy orthodontic wire is optimum force characteristics including the preferred low force magnitude and force constancy over a period of time. However it has been found in practice that beta titanium alloys exhibit creep over a period of time and this is undesirable in orthodontic wires which are intended to maintain shape over substantial periods.

It is an object of the present invention to provide a medical/dental/veterinary alloy for use in treatment of living vertebrates and which maintains or develops desirable properties over a period of time.

It is an object of a first particular aspect of-the present invention to provide an orthodontic wire which enables maintenance or development of desirable properties of the wire over a period of time. A further object is to provide an orthodontic appliance using such a wire.

It is an object of a second particular aspect of the present invention to provide an orthodontic wire treatment method which will produce desirable properties in the wire after a substantial period of use.

It is a yet further particular object to provide a method of fabricating an orthodontic appliance having or developing desirable properties over a period of time.

It is an object of a further particular aspect of the present invention to provide a method of orthodontic treatment utilising the desirable properties arising from the orthodontic wire treatment of the first aspect of the present invention.

According to the first aspect of the present invention there is provided a medical/dental/veterinary alloy for use in treatment of living vertebrates in which the alloy is used in an article located within body tissues or body cavities, the alloy comprising a titanium alloy having an alpha/beta crystalline structure or a near alpha crystalline structure. The titanium alloy comprises greater than 5% alpha stabilising components, the wire being maintained below the beta transus i.e. the minimum temperature at which substantially pure beta crystalline phase can exist, so as not to adopt the beta crystalline phase to any substantial extent. The alpha phase of an alloy has a hexagonal close packed crystalline structure, whereas the beta phase comprises a body centred cubic crystalline structure. A near alpha titanium alloy has greater than 5% by weight alpha stabilising ingredients and less than 2% beta stabilising ingredients.

In one possible embodiment of a near alpha titanium alloy there is provided a titanium alloy having greater than 5% aluminium, aluminium being an alpha stabilising ingredient. The preferred level of the aluminium component of the alloy is in excess of 7%. In one possible embodiment the alloy composition comprises a titanium alloy having about 8% aluminium, about 1% molybdenum and about 1% vanadium (vanadium being a beta stabilising element).

An embodiment of the alloy comprising an alpha beta titanium alloy preferably comprises, in addition to greater than 5% alpha stabilising ingredient(s), in excess of 2% beta stabilising ingredient(s). For example the beta stabilising ingredient may comprise vanadium. A suitable alloy may comprise a titanium alloy having aluminium present in an amount of about 6% and vanadium about 4% such an alpha beta alloy being commercially available under the designation IMI titanium 318).

The advantages of the alpha/beta titanium alloy and particularly the near alpha titanium alloy having less than 2% beta stabilising components, is a substantially improved creep resistance together with a capacity or Capability for the alloy to harden or become embrittled with age in an aqueous environment containing hydrogen such as free hydrogen ions. This latter advantage of hardening or embrittlement is believed to be a result of hydrogen being absorbed and this is facilitated in an aqueous environment. It is speculated that either the hardening or embrittlement arises from either the formation of brittle plates of titanium hydride or from the diffusion of hydrogen particularly into the stressed regions of the crystalline structure. The formation of the hydride is promoted by the presence of aluminium.

The alpha beta alloys and particularly the near alpha titanium alloys having less than 2% beta stabilising components exhibit the hardening or embrittlement property with time in an aqueous hydrogen contributing environment. The hardening or embrittlement is believed to proceed to a greater extent in a given time for the near alpha titanium alloys according to early subjective evaluation. The hardening property is an unexpected property not common to titanium alloys in general and particularly not appearing to be a property of beta titanium alloys. The property has particular advantages medical, dental and veterinary uses and particularly for for orthodontic uses as will be explained below.

The invention will be particularly described in relation to orthodontic use, but the handling process is believed to make the alloy suitable for uses such as orthopaedic wires used to locate and retain bones during healing of fractured bones, implanted metal pin or other articles which may need some formability during placement but are desirably hard in the longer term. The examples of results and uses described suggest wider medical, dental and veterinary applicability of the alloy as will be readily understood from the description.

An alpha beta titanium alloy having an initial hydrogen content of about 70 ppm was used in a wire for orthodontic treatment of several patients for about three to four months. After that period of time in the patients' mouths, i.e. in an aqueous hydrogen containing and contributing environment, the wires were tested for hydrogen content by melting and collecting and analysing the gases yielded up. All wires showed a significant increase in hydrogen content: one from 70 ppm to 120 ppm; several from 70 ppm to about 180 ppm; and one from 70 ppm to about 240 ppm. Generally at least a doubling of hydrogen content was found.

The orthodontic wire composition may be provided in a round cross section, a generally rectangular cross section or a square cross section. The generally rectangular or square cross sections are preferred for patient comfort and enabling re-positioning by the. orthodontist. A suitable rectangular configuration has cross sectional dimensions of 0.018×0.026 inches and a square wire may be 0.020 inches square.

The method of orthodontic wire treatment according to that aspect of the present invention comprises providing an orthodontic wire having a composition as outlined above and exposing that wire to an aqueous hydrogen contributing substance over a period of time so as to progressively harden or embrittle the wire over that period of time. The treatment may comprise exposing the wire fashioned, shaped or used in an orthodontic appliance and in use in a patient's mouth to an aqueous hydrogen containing and contributing substance to progressively harden the wire, The hardening of the wire in use enables the wire to be, used to apply a force to teeth so as to promote movement of the roots of the teeth in accordance with the orthodontist's treatment plan. In particular, the wire hardening as a result of the treatment process over a period of time thereby progressively lessens the force on teeth which have moved over that period of time towards their final desired positions determined at the time of installation of the wire, but generally maintains or increases the force on teeth (such as back teeth having larger roots) requiring larger or longer duration forces to effect tooth movement.

In the case of an orthodontic wire being used as an arch wire, a wire having the composition according to the present invention has good spring back properties so as to be capable of moving teeth over distances without the need to remove the wire for reactivation or reforming. Also the wire has good formability properties enabling the placement of bends within the wire. The hardening or embrittlement of the wire following installation and exposure to aqueous hydrogen contributing compositions over a period of time such as several weeks or months, is an unexpected and particularly advantageous property compared to beta titanium alloys and other known orthodontic wire compositions as mentioned above.

The treatment of the orthodontic wire in use may comprise administration of aqueous acidic or other hydrogen contributing substances to the wire such as by mouth washes or administration by means of swabbing or daubing the wires in situ with the aqueous solution.

The method of orthodontic wire treatment may include the further step of treating portion(s) of the wire(s) to inhibit localised hardening or embrittlement of the wire as a result of exposure to aqueous hydrogen contributing compositions over a period of time. The treatment may be carried out before initial placement of the wire in the patient's mouth so that some portion(s) do not harden, or harden to a lesser extent. This treatment may be desirable to enable reshaping of portions of an orthodontic wire, particularly the ends which are cinched, after a period of use without the embrittlement causing breaking of cinched ends upon re-straightening during reshaping the wire.

The treatment to inhibit hardening preferably comprises a treatment to inhibit hydrogen absorption by the alloy. One possible treatment comprises heating the portion to be made hydrogen resistant to create an oxide coating to inhibit hydrogen absorption. The heating is preferably carried out at a relatively low temperature (but above room or normally encountered temperatures in the mouth), e.g. to say 600° C. to 700° C. This temperature is believed sufficient to cause oxygen to take up interstitial positions at least to a number of atomic layers and between the metal particularly titanium atoms in the alloy which are the positions otherwise occupied by hydrogen atoms over the orthodontic treatment period. The heating is preferably of short duration, e.g. in the order of a few seconds so that surface oxidation only is effected. The heating may be carried out, e.g. by flame, until the surface exhibits a blue colour which indicates the presence of oxidation. Heating is then stopped (with quenching if desired) to prevent continuing oxidation which may immediately embrittle the end. The surface oxidation is believed to itself be brittle but inhibits or prevents hydrogen take up which over the period of orthodontic treatment would produce a degree of embrittlement to make reshaping of the wire more difficult or impossible.

An alternative method of treatment to inhibit hydrogen absorption may comprise an anodising process of the surface of the portion(s) to be treated. The anodised layer or skin can be effective to inhibit hydrogen absorption into the alloy producing the hardening effects.

The method of fabricating an orthodontic appliance according to that aspect of this invention comprises shaping an orthodontic wire having a composition as outlined above, the shaping comprising bending the wire without substantial heating to adopt the required conformation, followed by installing the wire in a patient's mouth so as to be secured to the patient's teeth and coupled to at least one tooth so as to apply a force upon that tooth. If desired localised pre-treatment of portion(s) of the wire to inhibit hardening may be carried out as described above to allow re-shaping after a period in the mouth.

The treatment of the orthodontic wire to exhibit the property of hardening or embrittlement is preferably carried at relatively low temperature and preferably in the range of 30° C. to 50° C., most preferably at about 36° C.–40° C.

The storage of the orthodontic wire having the particular composition may be temperature sensitive and therefore it may be preferable to store the wire (before being used in the fabrication of an orthodontic appliance) at a relatively low temperature, e.g. between 5° C. and 20° C. The wire may also be preferably stored in a dry environment so as not to be in contact with moisture which may provide a medium for introduction of hydrogen thereby causing premature hardening.

The present invention also provides a method of orthodontic treatment comprising the installation of orthodontic wire having a composition as outlined above within a patient's mouth so as to be affixed to the patient's teeth and be coupled to at least one tooth to be moved under forces applied to that tooth by the wire, the method further including hardening of the wire over a period of time by exposing the wire to an aqueous hydrogen contributing substance by means of which the orthodontic wire is hardened or embrittled over a period of time which is significant compared to the orthodontic treatment period. Pre-treatment of portion(s) to inhibit hardening as described above may be carried out before installation to enable later re-shaping of such portion(s).

As an example of use of the wire according to the present invention, and being used in a ribbon arch mode,, to place torque in the wire for a standard case, the torque can be wiped in for the anteriors when the anterior arch form is wiped in. Then with the aid of two pairs of pliers, the person installing the wire can crank out the buccal torque mesial to the cuspids. Molar offsets and other offsets can be placed to level and align the teeth. If the molars are awry, then bands can be placed on the second molars and the archwire passed through both sets of tubes. It has been found that there are less problems with retention when finishing archwires are routinely used. However the wires have great benefits where one needs good control to place the teeth precisely (compared to letting them settle) in such situations as cleft palate, cases which require prosthetic replacement such as Maryland bridges and for orthognathic surgery.

The wires can be held in with T-pins, the heads of which may also be used for attaching the patient's elastics. If desirable, shoe-hooks can be incorporated. These can be bent buccally in first instance, and then cranked vertically (gingivally)—again with two pliers, mesially and distally to the shoe-hooks. The wires are then cinched slowly.

The orthodontic wire according to the present invention when treated and used according to the process aspects of the present invention hardens in the mouth over a period of several weeks or months. This is ideal compared to other wires which soften over time. The hardening means that the wire is gentle on the shallower front teeth before reaching force levels for the larger back teeth. Also, compared to beta titanium wire, the alpha/beta, and particularly the near alpha titanium wire does not exhibit substantial creep.

It is to be understood that various alterations, modifications and/or additions may be made to the features of the possible and preferred embodiment(s) of the invention as herein described without departing from the scope of the invention as defined in the appended claims.

We claim:

1. A method of treatment of an orthodontic wire which is fashioned and used in an orthodontic appliance and which is in use in the mouth of a patient, the wire comprising a titanium alloy having a crystalline structure selected from the group consisting of an alpha/beta crystalline structure and a near alpha crystalline structure, said alloy comprising greater than 5% alpha stabilizing components and maintained below its beta transus, said beta transus being defined as the minimum temperature at which substantially pure beta phase can exist, so that said titanium alloy does not adopt a beta crystalline phase to any substantial extent, the method comprising applying an aqueous hydrogen contributing substance to said appliance within the patient's mouth over a period of time so as to harden or stiffen said wire progressively over said period of time thereby progressively lessening the force on teeth which have moved over said period of time towards their final desired positions determined at the time of installation of the wire and the appliance, the hardening or stiffening of the wire generally maintaining or increasing the force on teeth requiring larger forces or longer duration forces to effect movement of such teeth.

2. A method of orthodontic wire treatment as claimed in claim 1 and further including the step of treating a portion of the orthodontic wire to inhibit localized hardening or embrittlement of said portion of the wire as a result of exposure to the aqueous hydrogen contributing substance over the period of time.

3. A method of orthodontic wire treatment as claimed in claim 2 wherein the step of treating the portion of the wire comprises heating of said portion to be made resistant to hardening so that the heating creates an oxide coating at the heated portion of the wire.

4. A method of orthodontic wire treatment as claimed in claim 3 wherein the heating is carried out to a temperature of between 600° C. and 700° C.

5. A method of orthodontic wire treatment as claimed in claim 3 wherein the heating is carried out for a duration in the order of a few seconds so that surface oxidation only is effected.

6. A method of orthodontic wire treatment as claimed in claim 3 wherein the heating is carried out until the surface of the wire at the portion being heated exhibits a blue color indicating the presence of oxidation, the heating then being stopped to prevent further oxidation.

7. A method of orthodontic wire treatment as claimed in claim 2 wherein the step of treating the portion of the wire comprises anodising the surface of the portion.

8. A method of orthodontic wire treatment as claimed in claim 1 wherein the exposure of the aqueous hydrogen contributing substance to the orthodontic wire is carried out at a temperature of from 30° C. to 50° C.

9. A method of orthodontic treatment comprising the steps of:
shaping an orthodontic wire to form an orthodontic appliance, the shaping comprising bending the wire without substantial heating to adopt the required conformation, the orthodontic wire comprising a titanium alloy having a crystalline structure selected from the group consisting of an alpha/beta crystalline structure and a near alpha crystalline structure, said alloy comprising greater than 5% alpha stabilizing components and being maintained below its beta transus, said beta transus being defined as the minimum temperature at which substantially pure beta phase can exist, so that said titanium alloy does not adopt a beta crystalline phase to any substantial extent;
installing the orthodontic appliance in the mouth of a patient so as to secure it to at least one tooth of the patient with said wire being coupled to said at least one tooth so as to apply a force to that tooth; and
applying an aqueous hydrogen contributing substance to the appliance within the patient's mouth over a period of time so as to harden or stiffen said wire progressively over said period of time.

10. A method of orthodontic treatment as claimed in claim 9 and including the further step of pre-treating a portion of the orthodontic wire prior to the step of installing the orthodontic appliance, the step of pre-treating being carried out to inhibit localized hardening or embrittlement of said portion of the wire as a result of exposure to the aqueous hydrogen contributing substance over the period of time.

11. A method of orthodontic treatment as claimed in claim 10 wherein the step of pre-treating the portion of the wire comprises heating of said portion to be made resistant to hardening so that the heating creates an oxide coating at the heated portion of the wire.

12. A method of orthodontic treatment as claimed in claim 10 wherein the step of pre-treating the portion of the wire comprises anodizing the surface of the portion.

13. A method of orthodontic treatment comprising the steps of:
shaping an orthodontic wire to form an orthodontic appliance, the shaping comprising bending the wire without substantial heating to adopt the required conformation, the orthodontic wire comprising a titanium alloy having a crystalline structure selected from the group consisting of an alpha/beta crystalline structure and a near alpha crystalline structure, said alloy comprising greater than 5% alpha stabilizing components and being maintained below its beta transus, said beta transus being defined as the minimum temperature at which substantially pure beta phase can exist, so that said titanium alloy does not adopt a beta crystalline phase to substantial extent;
installing the orthodontic appliance in the mouth of a patient so as to couple said wire to at least one tooth of the patient so as to apply a force to that tooth to move that tooth during a desired period of orthodontic treatment; hardening of the orthodontic wire over a period of time by exposing the wire to an aqueous hydrogen contributing substance whereby the orthodontic wire is hardened or stiffened over said period of time, said period of time being a substantial proportion of said desired period of orthodontic treatment of the patient.

14. A method of orthodontic treatment as claimed in claim 13 wherein a portion of the orthodontic wire is pre-treated to inhibit hardening or embrittlement of said portion of the wire as a result of exposure to the aqueous hydrogen contributing substance over said period of time, the method or orthodontic treatment further comprising the step of reshaping said portion at least one time during said period of orthodontic treatment so as to adjust the magnitude and/or direction of force being applied by the orthodontic wire to said at least one tooth.

15. A method of orthodontic treatment as claimed in claim 13, wherein said alpha stabilizing components comprise aluminum.

16. A method of orthodontic treatment comprising the steps of:
shaping an orthodontic wire to form an orthodontic appliance, the shaping comprising bending the wire without substantial heating to adopt the required conformation, the orthodontic wire comprising a titanium alloy having a crystalline structure selected from the group consisting of an alpha/beta crystalline structure and a near alpha crystalline structure, said alloy comprising greater than 5% alpha stabilizing components and being maintained below its beta transus, said beta transus being defined as the minimum temperature at which substantially pure beta phase can exist, so that said titanium alloy does not adopt a beta crystalline phase to substantial extent;
installing the orthodontic appliance in the mouth of a patient so as to couple said wire to at least one tooth of the patient so as to apply a force to that tooth to move that tooth during a desired period of orthodontic treatment;
hardening of the orthodontic wire over a period of time by exposing the wire to an aqueous hydrogen contributing substance whereby the orthodontic wire is hardened or stiffened over said period of time, said period of time being a substantial proportion of said desired period of orthodontic treatment of the patient;
pre-treating a portion of the orthodontic wire to inhibit hardening or embrittlement of said portion of the wire as a result of exposure to the aqueous hydrogen contributing substance over said period of time; and
reshaping said portion at least one time during said period of orthodontic treatment so as to adjust the magnitude and/or direction of force being applied by the orthodontic wire to said at least one tooth.

* * * * *